(12) United States Patent
Makino et al.

(10) Patent No.: US 6,380,234 B1
(45) Date of Patent: *Apr. 30, 2002

(54) STABILIZED PHARMACEUTICAL COMPOSITION AND ITS PRODUCTION

(75) Inventors: Tadashi Makino; Tetsuro Tabata, both of Osaka; Shin-Ichiro Hirai, Kyoto, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/924,234

(22) Filed: Aug. 8, 2001

Related U.S. Application Data

(62) Division of application No. 09/588,956, filed on Jun. 7, 2000, now Pat. No. 6,296,875, which is a division of application No. 09/429,957, filed on Oct. 29, 1999, now Pat. No. 6,123,962, which is a division of application No. 09/196,664, filed on Nov. 19, 1998, now Pat. No. 6,017,560, which is a continuation of application No. 08/810,951, filed on Feb. 27, 1997, now Pat. No. 5,879,708, which is a continuation of application No. 08/488,152, filed on Jun. 7, 1995, now Pat. No. 5,639,478, which is a continuation of application No. 08/120,867, filed on Sep. 10, 1993, now Pat. No. 5,433,959, which is a continuation of application No. 07/793,091, filed on Nov. 15, 1991, now abandoned, which is a division of application No. 07/575,897, filed on Aug. 31, 1990, now Pat. No. 5,093,132, which is a continuation of application No. 07/014,303, filed on Feb. 13, 1987, now Pat. No. 5,045,321.

(30) Foreign Application Priority Data

Feb. 13, 1986 (JP) ................................ 12-29567
Feb. 21, 1986 (JP) ................................ 12-38059

(51) Int. Cl.⁷ ........................ A61K 31/415; A61K 9/30; A61K 33/12; A61K 33/10; A61K 33/08

(52) U.S. Cl. ........................ 514/394; 514/395; 514/925; 514/927; 424/475; 424/495; 424/683; 424/686; 424/692

(58) Field of Search ................................ 424/475, 495, 424/683, 686, 692; 514/394, 395, 925, 927

(56) References Cited

U.S. PATENT DOCUMENTS

| | | | |
|---|---|---|---|
| 2,880,136 A | 3/1959 | Gore ........................... | 424/686 |
| 4,045,563 A | 8/1977 | Bernisson .................... | 514/338 |
| 4,137,325 A | 1/1979 | Sellstedt et al. ............ | 514/538 |
| 4,255,431 A | 3/1981 | Junggren et al. ........... | 514/338 |
| 4,563,455 A | 1/1986 | Ueda et al. ................. | 514/394 |
| 4,634,710 A | 1/1987 | Fischli et al. ............... | 514/338 |
| 4,666,919 A | 5/1987 | Ueno et al. ................. | 514/970 |
| 4,686,230 A | 8/1987 | Rainer et al. ............... | 514/338 |
| 4,689,333 A | 8/1987 | Nohara et al. .............. | 514/338 |
| 4,767,769 A | 8/1988 | Hockley et al. ............. | 514/322 |
| 4,772,619 A | 9/1988 | Adelstein .................... | 514/338 |
| 4,786,505 A | 11/1988 | Lovgren et al. ............ | 424/468 |
| 4,824,856 A | 4/1989 | Okabe et al. ............... | 514/395 |
| 4,853,230 A | 8/1989 | Lovgren et al. ............ | 424/466 |
| 5,045,321 A | 9/1991 | Makino et al. .............. | 424/475 |
| 5,093,132 A | 3/1992 | Makino et al. .............. | 424/475 |
| 5,433,959 A * | 7/1995 | Makino et al. .............. | 424/475 |
| 5,639,478 A | 6/1997 | Makino et al. .............. | 424/475 |

FOREIGN PATENT DOCUMENTS

| | | |
|---|---|---|
| DE | 1034327 | 7/1958 |
| DE | 3427787 | 1/1986 |
| EP | 0045200 | 2/1982 |
| EP | 64283 | 11/1982 |
| EP | 0080602 | 6/1983 |
| EP | 0124495 | 11/1984 |
| EP | 0174726 | 3/1986 |
| EP | 0175464 | 3/1986 |
| EP | 244380 | 11/1987 |
| EP | 247983 | 12/1987 |
| FR | 2227856 | 11/1975 |
| GB | 2134523 | 8/1984 |
| JP | 58-201726 | 11/1983 |
| JP | 59-167587 | 9/1984 |
| JP | 60-19175 | 1/1985 |
| JP | 61-85383 | 4/1986 |
| JP | 320215 | 1/1991 |

OTHER PUBLICATIONS

Central Patents Index, "Stabilization of Preparations Containing Ampicilin and Dicloxacillin/Cephalexin . . . ", JA–0869565, May 9, 1975, Derwent Publication, Ltd., London, England (Mar. 2, 1976).

(List continued on next page.)

Primary Examiner—Kevin E. Weddington
(74) Attorney, Agent, or Firm—Merchant & Gould PC

(57) ABSTRACT

The pharmaceutical composition of the invention, which comprises a benzimidazole compound of the formula

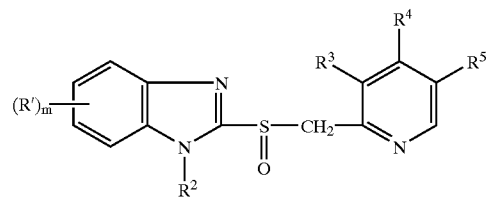

wherein $R^1$ is hydrogen, alkyl, halogen, cyano, carboxy, carboalkoxy, carboalkoxyalkyl, carbamoyl, carbamoylalkyl, hydroxy, alkoxy, hydroxyalkyl, trifluoromethyl, acyl, carbamoyloxy, nitro, acyloxy, aryl, aryloxy, alkylthio or alkylsulfinyl, $R_2$ is hydrogen, alkyl, acyl, carboalkoxy, carbamoyl, alkylcarbamoyl, dialkylcarbamoyl, alkylcarbonylmethyl, alkoxycarbonylmethyl or alkylsulfonyl, $R^3$ and $R^5$ are the same or different and each is hydrogen, alkyl, alkoxy or alkoxyalkoxy, $R^4$ is hydrogen, alkyl, alkoxy which may optionally be fluorinated, or alkoxyalkoxy, and m is an integer of 0 through 4, and a basic inorganic salt stabilizing agent, is physically stable. Magnesium and calcium basic inorganic salt stabilizing agents are particularly useful.

3 Claims, No Drawings

OTHER PUBLICATIONS

European Search Report corresponding to European Application 87 30 1244.

Rote Liste, 1985 Ref. No. 59152.

E. Schroder et al., "Arzneimittelchemie II", vol. 2, 1976, pp. 307–308.

*Handbook of Nonprescription Drugs*, Fifth, Ed., Pub. 1977, American Pharm. Assoc., pp. 7–10.

*Journal of the Chemical Society, Chemical Communications*, pp. 125–127 (1986)(translation provided).

Hydroxypropyl Methycellulose, TC–5. published by Shin–Etsu Chemical in 1975 and 1978 (translation provided).

In Up–to–Date Pharmaccurical Technology Series "No.1", (1968). "Coating of Drugs", pp. 246, 247 and 250 (translation provided).

Communication of a Notice of Opposition.

Board Decision No. 57—shinpan–21724.

Hersey, "Ordered Mixing: A New Concept in Powder Mixing Practice", *Powder Technology*, vol. 11 (1975), pp. 41–44.

"Seizai–gaku", pp. 115–116, Ed. by Yoshinobu Nakai et al., pub. by Nazando.

Hersey, "Preparation and Properties of Ordered Mixtures", *Australian Journal of Pharmaceutical Sciences*, Feb. 1977, vol. 6, No. 1, pp. 29–32.

Pilbrandt et al., "Development of an Oral Formulation Omeprazole", pp. 113–120.

*The United States Pharmacopeia*, 1985, pp. 1277–1278.

Shotton et al., "Studies on Mixing Cohesive Powders", Science Communications. *J. Pharm. Pharmac*, 1971, vol. 23, Suppl. 261S, pp. 260–261.

Malmquist et al., "Studies on Direct Compression of Tables", *Acta Pharm. Suec.*, vol. 21, pp. 9–20, 1984.

Opposition filed by AB Astra on Aug. 16, 1991.

Brandstrom et al., "Chemical Reactions of Omeprazole and Omeprazole Analogues", *ActaChemical Scandinavca*, vol. 43, 1989, pp. 536–548.

Crooks et al., "Ordered Mixing in Direct Compression of Tablets", *Powder Technology*, vol. 14, 1976, pp. 161–167.

Westerberg, "Studies on Ordered Mixtures for fast Release and Dissolution of Drugs with Low Aqueous Solubility", Department of Pharmaceutics, UPPSALA University, 1992, pp. 11–12.

Benjamin et al., "Stabilization of Sulconazole Nitric in a Topic Powder Formulation", *International Journal of Pharmaceutics*, vol. 14, 1983, pp. 209–221.

Board Decision of No. 54–Shinpan–11599.

Experiment of Mr. Yasumura.

Experiment of Mr. Oishi.

Communication Pursuant to Article 115(2) EPC.

\* cited by examiner

STABILIZED PHARMACEUTICAL COMPOSITION AND ITS PRODUCTION

This application is a Divisional of application Ser. No. 09/588,956, filed Jun. 7, 2000 now U.S. Pat. No. 6,296,875 (allowed May 9, 2001) which is a Divisional of application Ser. No. 09/429,957, filed Oct. 29, 1999 (now U.S. Pat. No. 6,123,962), which is a Divisional of application Ser. No. 09/196,664, filed Nov. 19, 1998 (now U.S. Pat. No. 6,017,560), which is a continuation of application Ser. No. 08/810,951, filed Feb. 27, 1997 (now U.S. Pat. No. 5,879,708), which is a continuation of Ser. No. 08/488,152, filed Jun. 7, 1995 (now U.S. Pat. No. 5,639,478), which is a continuation of Ser. No. 08/120,867, filed on Sep. 10, 1993 (now U.S. Pat. No. 5,433,959), which is a continuation of Ser. No. 07/793,091, filed Nov. 15, 1991 (now abandoned), which is a divisional of Ser. No. 07/575,897, filed Aug. 31, 1990 (now U.S. Pat. No. 5,093,132), which is a continuation of Ser. No. 07/014,303, filed Feb. 13, 1987 (now U.S. Pat. No. 5,045,321) which application(s) are incorporated herein by reference.

This invention relates to a pharmaceutical composition which comprises 2-[(2-pyridyl)methylsulphinyl] benzimidazole or a derivative thereof (hereinafter sometimes referred to collectively as "benzimidazole compounds"), particularly the derivatives 2-[[3-methyl-4-(2,2,2-trifluoromethoxy)-2-pyridyl]methylsulfinyl] benzimidazole and 5-methoxy-2-[(4-methoxy-3,5-dimethyl-2-pyridyl)methylsulfinyl]benzimidazole, or a pharmaceutically acceptable salt thereof, which is useful as an antiulcer agent. The composition is stabilized by incorporation of an effective amount of a basic inorganic salt stabilizing agent, with basic inorganic salts of magnesium, calcium, potassium and sodium being useful, the magnesium can calcium salts being preferred.

Certain benzimidazole compounds are recently under clinical study as gastric acid secretion inhibitors. They serve as therapeutic agents for digestive ulcer. Their principal pharmacological effect consists in gastric acid secretion suppression based on ($H^{30}+K^+$)-ATPase inhibition and is more potent and durable as compared with histamine $H_2$ receptor antagonists such as cimetidine and ranitidine. They also have gastric mucosa protecting activity. Therefore, they have attracted attention as next-generation potent therapeutic agents for digestive ulcer.

Those benzimidazole compounds which are described in Japanese Unexamined Patent laid open Nos. 62275/77, 141783/79, 53406/82, 135881/83, 192880/83 and 181277/84, corresponding to U.S. Pat. No. 4,045,563, U.S. Pat. No. 4,255,431, European Patent Publication No. 45,200, U.S. Pat. No. No. 4,472,409, European Patent Publication No. 5,129 and G.B. Patent Publication No. 2,134,523A, respectively, among others are known to have antiulcer activity.

These compounds, however, are poor in stability. In solid state, they are susceptible to heat, moisture and light and, in aqueous solution or suspension, their stability decreases with decreasing pH. In dosage forms, i.e. tablets, powders, fine granules, granules and capsules, said compounds are apt to interact with other components contained in said dosage forms and accordingly are in less stable state as compared with the case where they occur alone. Thus, the content decreases and the color changes significantly in the manufacturing process of dosage form and with the lapse of time. Microcrystalline cellulose, polyvinylpyrrolidone (PVP), carboxymethylcellulose calcium, polyethylene glycol 6000 and Pluronic F68 (polyoxyethylene-polyoxypropylene copolymer), for instance are dosage form components adversely affecting the stability of said compounds. Furthermore, in the case of coated tablets and coated granules among the above dosage forms, enteric coating bases such as cellulose acetate phthalate, hydroxypropylmethylcellulose acetate succinate and Eudragit (methacrylic acid-acrylic acid copolymer) have poor compatibility with said compounds and cause content decrease and color change. Nevertheless, one or more of these components or ingredients, which, as mentioned above, can produce adverse effects on the stability of said compounds, are essential in the manufacture of oral preparations and therefore difficulties are inevitably encountered in dosage form manufacture.

The prior art avoids the above-mentioned stability problem by using said benzimidazole compounds in a salt form, say in the form of a lithium, sodium, potassium, magnesium, calcium or titanium salt [Japanese Unexamined Patent laid open No. 167587/84 (European Patent Publication No. 124,495A)]

However, the above prior art method requires, for the stabilization of the benzimidazole compounds, a step of converting said compounds to such a salt form as mentioned above in advance.

In view of the above, the present inventors made investigations in an attempt to stabilize pharmaceutical preparations containing benzimidazole compounds and, as a result, have completed the present invention.

Thus, this invention relates to (1) A pharmaceutical composition which comprises 2-[(2-pyridyl)methylsulfinyl]benzimidazole or a derivative thereof, which has an antiulcer activity, and a basic inorganic salt of magnesium and/or a basic inorganic salt of calcium, and (2) A method of producing a stabilized pharmaceutical composition which comprises incorporating a basic inorganic salt of magnesium and/or a basic inorganic salt of calcium in a pharmaceutical composition containing 2-[(2-pyridyl-methylsulfinyl]benzimidazole or a derivative thereof, which has an antiulcer activity.

The benzimidazole compounds having an antiulcer activity which are to be used in the practice of the invention are those compounds which are described in the above-cited laid-open patent specifications, for instance and are represented by the formula

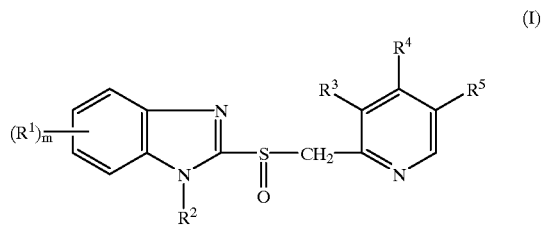

(I)

wherein $R^1$ is hydrogen, alkyl, halogen, cyano, carboxy, carboalkoxy, carboalkoxyalkyl, carbamoyl, carbamoylalkyl, hydroxy, alkoxy, hydroxyalkyl, trifluoromethyl, acyl, carbamoyloxy, nitro, acyloxy, aryl, aryloxy, alkylthio or alkylsulfinyl, $R^2$ is hydrogen, alkyl, acyl, carboalkoxy, carbamoyl, alkylcarbamoyl, dialkylcarbamoyl, alkylcarbonylmethyl, alkoxycarbonylmethyl or alkylsulfonyl, $R^3$ and $R^5$ are the same or different and each is hydrogen, alkyl, alkoxy or alkoxyalkoxy, $R^4$ is hydrogen, alkyl, alkoxy which may optionally be fluorinated, or alkoxyalkoxy, and m is an integer of 0 through 4.

The compounds of the formula(I) can be produced by the methods described in the above-cited laid-open patent specifications or modifications thereof.

In the following, brief mention is made of the substituents in those compounds which have the formula (I) and are already known.

Referring to $R^1$ in the above formula, $C_{1-7}$ alkyls may be mentioned as the alkyl represented by $R^1$; $C_{1-4}$ alkoxys as the alkoxy moiety of the carboalkoxy; $C_{1-4}$ alkoxys as the alkoxy moiety of the carboalkoxyalkyl and $C_{1-4}$ alkyls as the alkyl moiety; $C_{1-4}$ alkyls as the alkyl moiety of the carbamoylalkyl; $C_{1-5}$ alkoxys as the alkoxy; $C_{1-7}$ alkyls as the alkyl moiety of the hydroxyalkyl; $C_{1-4}$ alkanoyls as the acyl; phenyl as the aryl; phenyl as the aryl moiety of the aryloxy; $C_{1-6}$ alkyls as the alkyl moiety of the alkylthio; and $C_{1-6}$ alkyls as the alkyl moiety of the alkylsulfinyl.

Referring to $R^2$, $C_{1-5}$ alkyls may be mentioned as the alkyl represented by $R^2$; $C_{1-4}$ alkanoyls as the acyl; $C_{1-4}$ alkoxys as the alkoxy moiety of the carboalkoxy; $C_{1-4}$ alkyls as the alkyl moiety of the alkylcarbamoyl; $C_{1-4}$ alkyls as each of the alkyl moieties of the dialkylcarbamoyl; $C_{1-4}$ alkyls as the alkyl moiety of the alkylcarbonylmethyl; $C_{1-4}$ alkoxys as the alkoxy moiety of the alkoxycarbonylmethyl; and $C_{1-4}$ alkyls as the alkyl moiety of the alkylsulfonyl.

Referring to $R^3$, $R^4$ and $R^5$, $C_{1-4}$ alkyls may be mentioned as the alkyl represented by any of them; $C_{1-8}$ alkoxys as the alkoxy; and $C_{1-4}$ alkoxys as each of the alkoxy moieties of the alkoxyalkoxy.

Referring to $R^4$, $C_{1-8}$ alkoxys may be mentioned as the alkoxy, which may optionally be fluorinated.

Among those compounds of the above forumula (I), (1) the compounds of which $R^1$ is hydrogen, methoxy or trifluoromethyl, $R^2$ is hydrogen, $R^3$ and $R^5$ are the same or different and each is hydrogen or methyl, $R^4$ is fluorinated $C_{2-5}$ alkoxy and m is 1, (2) the compounds of which $R^1$ is hydrogen, fluorine, methoxy or trifluoromethyl, $R^2$ is hydrogen, $R^3$ is hydrogen or methyl, $R^4$ is $C_{3-8}$ alkoxy, $R^5$ is hydrogen and m is 1, and (3) the compounds of which $R^1$ is hydrogen, fluorine, methoxy or trifluoromethyl, $R^2$ is hydrogen, $R^3$ is $C_{1-8}$ alkoxy, $R^4$ is $C_{1-8}$ alkoxy which may be fluorinated, $R^5$ is hydrogen and m is 1.

Detailed mention is now made of the substituents in such novel compounds.

Referring to $R^3$, the lower alkyl represented thereby is preferably $C_{1-8}$ lower alkoxy such as methoxy, ethoxy, propoxy, isopropoxy, butoxy, isobutoxy, pentyloxy, hexyloxy, heptyloxy or octyloxy and more preferably $C_{1-4}$ lower alkoxy.

Referring to $R^4$, $C_{1-8}$ lower alkoxys may be mentioned as the lower alkoxy, which may optionally be fluorinated, and preferred examples are as mentioned above for $R^3$. As the fluorinated lower alkoxy, there may be mentioned, for example, 2,2,2-trifluoroethoxy, 2,2,3,3,3-pentafluoropropoxy, 1-(trifluoromethyl)-2,2,2-trifluoroethoxy, 2,2,3,3-tetrafluoropropoxy, 2,2,3,3,4,4,4-heptafluorobutoxy and 2,2,3,3,4,4,5,5-octafluoropentoxy, and fluorinated $C_{2-4}$ lower alkoxys are preferred.

The position of $R^1$ is position 4 or position 5, preferably position 5.

Some methods of producing the above novel compounds [hereinafter referred to as "compounds of formula (I')"] are described below.

Said compounds can be produced by subjecting a compound of the formula

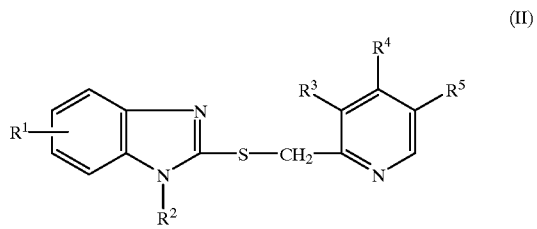

(II)

wherein $R^1$–$R^5$ are as defined above, to oxidation.

The oxidizing agent to be used is, for example, meta-chloroperbenzoic acid, peracetic acid, trifluoroperacetic acid, permaleic acid or the like peracid, sodium bromite or sodium hypochlorite. Examples of the solvent to be used in carrying out the reaction are halogenated hydrocarbons such as chloroform and dichloromethane, ethers such as tetrahydrofuran and dioxane, amides such as dimethylformamide, and water. These solvents may be used either singly or in admixture. Said oxidizing agent is used preferably in an amount approximately equivalent or slightly excessive relative to the compound (II). Thus, said agent is used in an amount of about 1–3 equivalents, more preferably about 1 to 1.5 equivalents. The reaction is carried out at a temperature from about 0° C. (ice cooling) to around the boiling point of the solvent used, generally at a temperature from about 0° C. (ice cooling) to room temperature, preferably at a temperature of about 0° C. to 10° C. The reaction time is generally about 0.1 to 24 hours, preferably about 0.1 to 4 hours.

The desired novel compounds (I') produced by the above reaction can be isolated and purified by conventional means such as recrystallization, chromatography and so on.

Said compounds may be converted to pharmacologically acceptable salts by conventional means. As such salts, there may be mentioned hydrochloride, hydrobromide, hydroiodide, phosphate, nitrate, sulfate, acetate and citrate, among others.

The novel compounds (II) can be produced by reacting a starting compound of the formula

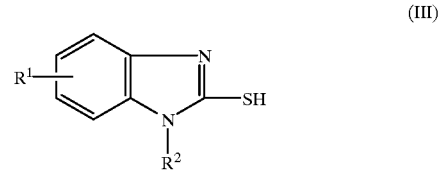

(III)

wherein $R^1$ and $R^2$ are as defined above, with a starting compound of the formula

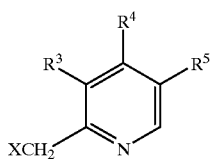

wherein $R^3$–$R^5$ are as defined above and X is a halogen atom.

The halogen atom represented by X is, for example, chlorine, bromine or iodine.

The reaction is carried out advantageously in the presence of a base. As said base, there may be mentioned alkali metal hydrides such as sodium hydride and potassium hydride, alkali metals such as metallic sodium, sodium alcoholates such as sodium methoxide and sodium ethoxide, alkali metal carbonates such as potassium carbonate and sodium carbonate, and organic amines such as triethylamine, among others. As the solvent to be used in carrying out the reaction, there may be mentioned, for example, alcohols such as methanol and ethanol, and dimethylformamide. The base is used generally in an amount slightly excessive relative to the equivalent amount but may also be used in large excess. Thus, it is used in an amount of about 2–10 equivalents, preferably about 2–4 equivalents. The above reaction is carried out generally at a temperature of about 0° C. to around the boiling point of the solvent used, preferably at about 20° C. to 80° C., for a period of about 0.2–24 hours, preferably about 0.5–2 hours.

Some methods of producing the starting compounds (IV) are described below.

Among the compounds (IV), those compounds wherein $R^3$ and $R^5$ are the same or different and each is hydrogen or methyl and $R^4$ is fluorinated $C_{2-5}$ alkoxy or $C_{3-8}$ alkoxy can be produced by the following process:

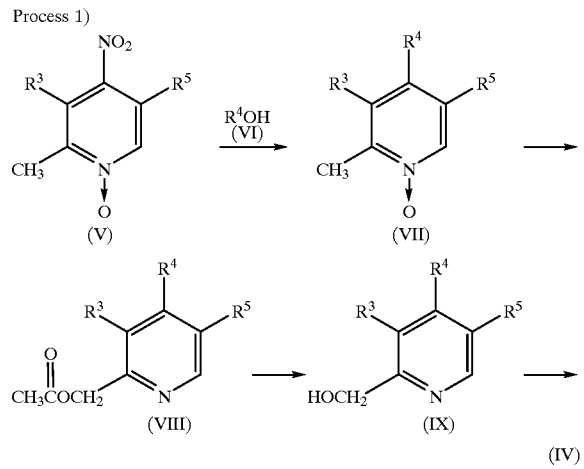

A nitro compound of the formula (V), wherein $R^3$ and $R^5$ are as defined above, is reacted with an alcohol derivative of the formula $R^{4'}OH$ (VI) wherein $R^{4'}$ is fluorinated $C_{2-5}$ alkyl or $C_{3-8}$ alkyl, in the presence of a base to give an alkoxy derivative of the formula (VII) wherein $R^3$, $R^4$ and $R^5$ are as defined above. The base to be used in carrying out the reaction includes, among others, alkali metals such as lithium, sodium and potassium, alkali metal hydrides such as sodium hydride and potassium hydride, alcoholates such as potassium t-butoxide and sodium propoxide, alkali metal carbonates and hydrogen carbonates such as potassium carbonate, lithium carbonate, sodium carbonate, potassium hydrogen carbonate and sodium hydrogen carbonate, and alkali metal hydroxides such as sodium hydroxide and potassium hydroxide. The alcohol derivative to be submitted to the reaction includes, among others, propanol, isopropanol, butanol, pentanol, hexanol, 2,2,2-trifluoroethanol, 2,2,3,3,3-pentafluoropropanol, 2,2,3,3-tetrafluoropropanol, 1-(trifluoromethyl)-2,2,2-trifluoroethanol, 2,2,3,3,4,4,4-heptafluorobutanol and 2,2,3,3,4,4,5,5-octafluoropentanol. While $R^{4'}OH$ itself may be used as a solvent in carrying out the reaction, ethers such as tetrahydrofuran and dioxane, ketones such as acetone and methyl ethyl ketone, acetonitrile, dimethylformamide and hexamethylphosphoric acid triamide, for instance, may also be used as solvents. An appropriate reaction temperature may be selected within the range of about 0° C. (ice cooling) to around the boiling point of the solvent used. The reaction time is about 1–48 hours.

Heating (about 80–120° C.) of the thus-obtained compound (VII) with acetic anhydride alone or in the presence of an inorganic acid such as sulfuric acid or perchloric acid gives an 2-acetoxymethylpyridine derivative of the formula (VIII) wherein $R^3$, $R^4$ and $R^5$ are as defined above. The reaction period is generally about 0.1–10 hours.

The subsequent alkaline hydrolysis of the compound (VIII) gives a 2-hydroxymethylpyridine derivative of the formula (IX). Sodium hydroxide, potassium hydroxide, potassium carbonate and sodium carbonate, for instance, are usable as alkalis, and methanol, ethanol and water, among others, are usable as solvents. The reaction is generally conducted at about 20–60° C. for about 0.1–2 hours.

The compound (IX) is further halogenated with a chlorinating agent such as thionyl chloride to give a 2-halomethylpyridine derivative of the formula (IV) wherein $R^3$, $R^4$ and $R^5$ are as defined above and X is chlorine, bromine and iodine. Usable as solvents are, for example, chloroform, dichloromethane and tetrachloroethane. The reaction is generally carried out at about 20–80° C. for about 0.1–2 hours.

The compound (IV) thus produced occurs in the form of a salt of hydrohalogenic acid corresponding to the halogenating agent used and it is generally preferable to subject said compound to reaction with the compound (III) immediately.

Among the compounds (V), those compounds wherein $R^3$ is $C_{1-8}$ lower alkoxy, $R^4$ is alkoxy which may optionally be fluorinated, and $R^5$ is hydrogen can be produced by the following process:

Process 2)

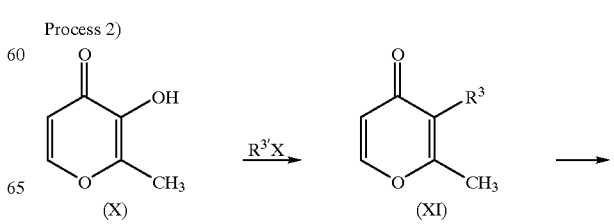

-continued

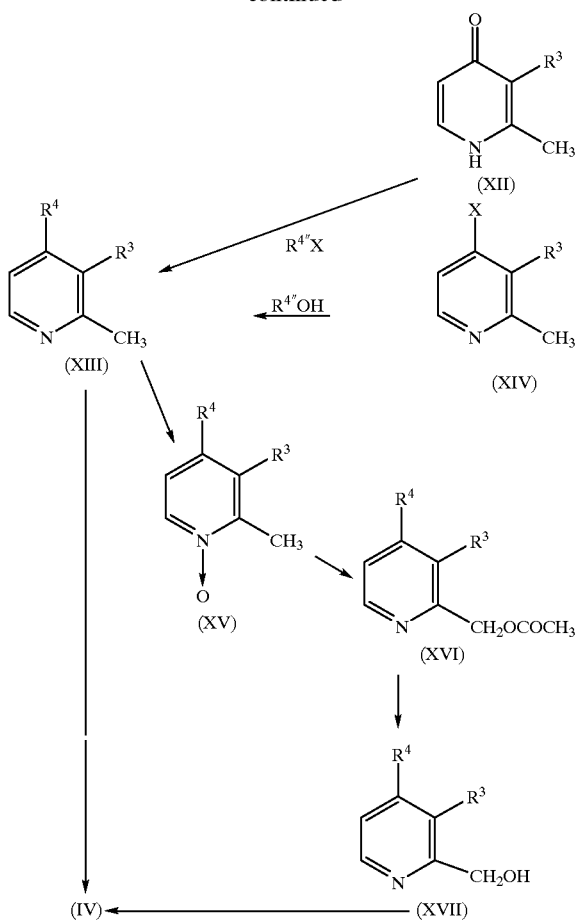

Thus, maltol (X) is reacted with a alkyl halide of the formula R³X in the presence of silver oxide, for instance, to give a compound of the formula (XI). Reaction of (XI) with aqueous ammonia gives a pyridone derivative of the formula (XII). Direct alkylation of the compound (XII) with an alkyl halide, or halogenation of (XII) with a halogenating agent such as phosphorus oxychloride followed by reaction of the resultant halo derivative (XIV) with a lower alcohol of the formula R⁴"OH in the presence of a base gives a compound of the formula (XIII). The compound (XIII) can be converted to the compound (IV) by direct halogenation with N-bromosuccinimide or chlorine, for instance. The compound (XIII) may also be converted to the compound (IV) by oxidizing the same with an oxidizing agent such as m-chloroperbenzoic acid, reacting the resulting compound (XV) with acetic anhydride, hydrolyzing the resulting compound (XVI) and halogenating the resulting compound (XVII) with a halogenating agent such as thionyl chloride.

The alkyl halide to be used in the production of the compound (XI) includes, among others, methyl iodide, ethyl iodide, propyl iodide, isopropyl iodide, butyl iodide, pentyl iodide and hexyl iodide, and the alkyl halide to be used in the production of the compound (XIII) further includes, in addition to those mentioned above for use in the production of the compounds (XI), 2,2,2-trifluoroethyl iodide, 2,2,3,3, 3-pentafluoropropyl iodide 2,2,3,3-tetrafluoropropyl iodide, 1-(trifluoromethyl)-2,2,2-trifluoroethyl iodide, 2,2,3,3,4,4,4-heptafluorobutyl iodide and 2,2,3,3,4,4,5,5-octafluoropentyl iodide, for instance. Such alkyl iodides are used in an amount of about 1–10 equivalents. Silver oxide, potassium carbonate, sodium carbonate or the like is used as a deacidifying agent and dimethylformamide, dimethylacetamide or the like is used as a solvent. The reaction is generally carried out at room temperature.

The halogenating agent to be used in the production of the compound (XIV) includes, among others, phosphorus oxychloride, phosphorus pentoxide and phosphorus tribromide and is used in an amount of 1 equivalent to a large excess. The reaction is carried out at a temperature of about 50–150° C. The alcohol to be used for the conversion of compound (XIV) to compound (XIII) includes methanol and ethanol and further those alcohol derivaitves mentioned for use in process 1) and is used in an amount of 1 equivalent to a large excess, and the base includes those sodium alcoholates and potassium alcoholates which correspong to the respective alcohols as well as potassium t-butoxide, sodium hydride and so forth. An appropriate reaction temperature may be selected within the range of room temperature to the boiling point of the solvent used.

For direct bromination of the compound (XIII) with N-bromosuccinimide, the reaction is preferably carried out under light irradiation, and carbon tetrachloride, chloroform, tetrachloroethane or the like is used as a solvent.

The oxidizing agent to be used for the conversion of compound (XIII) to compound (XV) includes, among others, peracids such as meta-chloroperbenzoic acid, peracetic acid, trifluoroperacetic acid and permaleic acid as well as hydrogen peroxide. Usable as solvents for the reaction are halogenated hydrocarbons such as chloroform and dichloromethane, ethers such as tetrahydrofuran and dioxane, amides such as dimethylformamide, acetic acid and water, for instance, and these can be used either singly or in admixture. Said oxidizing agent is preferably used in an amount of about 1 equivalent to an excess relative to the compound (XIII), more preferably about 1–10 equivalents. The reaction is carried out at a temperature of about 0° C. (ice cooling) to around the boiling point of the solvent used generally for a period of about 0.1–24 hours, preferably for about 0.1–4 hours.

The conversion of compound (XV) to compound (XVI) is effected by heating (at about 80–120° C.) the compound (XV) with acetic anhydride alone or in the presence of an inorganic acid such as sulfuric acid or perchloric acid and so on. The reaction period is generally 0.1–10 hours.

The alkali to be used in the alkaline hydrolysis of compound (XVI) to compound (XVII) includes, among others, sodium hydroxide, potassium hydroxide, potassium carbonate and sodium carbonate. Methanol, ethanol and water, for instance, may be mentioned as usable solvents. The reaction is generally carried out at a temperature of about 20–60° C. for a period of about 0.1–2 hours.

For the production of compound (IV) from compound (XVII), a chlorinating agent such as thionyl chloride or an organic sulfonic or organic phosphoric acid chloride such as methanesulfonyl chloride, p-toluenesulfonyl chloride or diphenylphosphoryl chloride is used. When a chlorinating agent such as thionyl chloride is used, it is used in an amount of 1 equivalent to a large excess relative to the compound (XVII) and a solvent such as chloroform, dichloromethane or tetrachloroethane is used, and the reaction is generally carried out at a temperature of about 20–80° C. for a period of about 0.1–2 hours. When an organic sulfonic or organic phosphoric acid chloride is used, it is used in an amount of 1 equivalent to a slight excess relative to the compound (XVII) and the reaction is generally carried out in the presence of a base. As usable bases, there may be mentioned organic bases such as triethylamine and tributylamine and inorganic bases such as sodium carbonate, potassium carbonate and sodium hydrogen carbonate. The base is used in an amount of 1 equivalent to a slight excess. As usable solvents, there may be mentioned, for example, chloroform, dichloromethane, carbon tetrachloride and acetonitrile. An appropriate reaction temperature and an appropriate reaction can be selected within the ranges of about 0° C. (ice cooling) to around the boiling point and several minutes to several hours, respectively.

The above-mentioned novel benzimidazole compounds have excellent gastric antisecretory activity, gastric mucosa-protecting activity and antiulcer activity but have low toxicity, so that they can be used in the treatment of digestive ulcers in mammals (e.g. mouse, rat, rabbit, dog, cat, human).

The basic inorganic salt stabilizing agents, which are to be used in accordance with the invention, are now described.

Especially useful basic inorganic salt stabilizing agents are basic inorganic salts of magnesium and calcium. Said basic inorganic salt of magnesium includes, among others, heavy magnesium carbonate, magnesium carbonate, magnesium oxide, magnesium hydroxide, magnesium metasilicate aluminate, magnesium silicate aluminate, magnesium silicate, magnesium aluminate, synthetic hydrotalcite $[Mg_6Al_2(OH)_{16} \cdot CO_3 \cdot 4H_2O]$ and aluminum magnesium hydroxide $[2.5MgO \cdot Al_2O_3 \cdot xH_2O]$ and said basic inorganic salt of calcium includes, among others, precipitated calcium carbonate and calcium hydroxide. Other basic inorganic salts useful as stabilizing agents include sodium and potassium basic inorganic salts such as potassium carbonate, sodium carbonate and sodium hydrogen carbonate, as well as aluminum basic inorganic salts such as aluminum silicate. It is only required of such basic inorganic salts to show basicity (pH of not less than 7) when they are in the form of a 1% aqueous solution or suspension.

Said basic inorganic salts may be used either singly or in combination of two or more species in an amount which may vary depending on the kinds thereof but generally lies within the range of about 0.3–20 parts by weight, preferably about 0.6–7 parts by weight, per part by weight of the benzimidazole compounds.

The composition of the invention may further contain such additives as vehicles (e.g. lactose, corn starch, light silicic anhydride, microcrystalline cellulose, sucrose), binders (e.g. α-form starch, methylcellulose, carboxymethylcellulose, hydroxypropylcellulose, hydroxypropylmethylcellulose, polyvinylpyrrolidone), disintegrating agents (e.g. carboxymethylcellulose calcium, starch, low substituted hydroxypropylcellulose), surfactants [e.g. Tween 80 (Kao-Atlas), Pluronic F68 (Asahi Denka; polyoxyethylene-polyoxypropylene copolymer], antioxidants (e.g. L-cysteine, sodium sulfite, sodium ascorbate), lubricants (e.g. magnesium stearate, talc), etc.

The composition of the invention is prepared by homogeneously admixing the above benzimidazole compound, the basic inorganic salt stabilizing agent, and the above additives.

The particle sizes of said benzimidazole compound and said inorganic salt are not especially critical in a condition that they can be homogeneously admixed. For example, preferable perticle size is about less than 100 um, more preferable one is about less than 20 um.

The moisture amount in the composition is preferably about 6–60%, more preferably about 20–40% as equibrium relative humidity (E.R.H.) The method of admixing is optional if the benzimidazole compound can finally be in contact with the basic inorganic salt stabilizing agent evenly. Thus, for example, the additives may be admixed with a mixture of the benzimidazole compound and the basic inorganic salt stabilizing agent as prepared by preliminary admixing, or the basic inorganic salt stabilizing agent may be added to a mixture of the benzimidazole compound and the additives as prepared by preliminary admixing.

Said mixture can be made up into dosage forms suited for oral administration, such as tablets, capsules, powders, granules and fine granules, by per se known means.

Tablets, granules and fine granules may be coated by a per se known method for the purpose of masking of the taste or providing them with enteric or sustained release property. Usable as coating agents are, for example, hydroxypropylmethylcellulose, ethylcellulose, hydroxymethylcellulose, hydroxypropylcellulose, polyoxyethylene glycol, Tween 80, Pluornic F68, cellulose acetate phthalate, hydroxypropylmethylcellulose phthalate, hydroxymethylcellulose acetate succinate, Eudragit (Röhm, West Germany; methacrylic acid-acrylic acid copolymer) and pigments such as titanium oxide and ferric oxide.

Tablets, granules, powders, fine granules and capsules can be produced by a conventional method (e.g. the method described in the 10th edition of the Japanese Pharmacopeia under General Rules for Preparations). Thus, for example, tablets are produced by adding the basic inorganic salt stabilizing agent to a mixture of the benzimidazole compound, vehicle and disintegrant, mixing, adding a binder, granulating the mixture, adding a lubricant etc. and tableting the resultant granular composition. Granules are produced by extrusion in approximately the same manner as in the production of tablets or by coating nonpareils, which contain sucrose and corn starch, with a mixture of benzimidazole compound, a basic inorganic salt stabilizing agent, and additives (e.g. sucrose, corn starch, crystalline cellulose, hydroxypropyl-cellulose, methylcellulose, hydroxypropylmethyl-cellulose, polyvinylpyrrolidone) Capsules are produced by mere mixing and filling. The dosage forms thus obtained show excellent stability with slight changes in appearance and little decreases in content even after storage for a long period of time.

The pharmaceutical composition of the present invention as obtained in the above manner exhibits excellent gastric antisecretory, gastric mucosa-protecting and antiulcer activities and has low toxicity and therefore can be used in the treatment of digestive ulcers in mammals (e.g. mouse, rat, rabbit, dog, cat, pig, human).

The pharmaceutical composition of the invention can be orally administered for the treatment of digestive ulcers in mammals in admixture with pharmacologically acceptable carriers, vehicles, diluents and so forth and in the form of capsules, tablets, granules and some other dosage forms, as mentioned hereinabove. The dose as the benzimidazole compound lies within the range of about 0.01 mg to 30 mg/kg/day, preferably about 0.1 mg to 3 mg/kg/day.

The following reference examples and working examples as well as the experimental examples described later herein illustrate the present invention in more detail but are by no means limitative of the present invention.

REFERENCE EXAMPLE 1

A mixture of 2,3-dimethyl-4-nitropyridine-1-oxide (2.0 g), methyl ethyl ketone (30 ml), 2,2,3,3,3-pentafluoropropanol (3.05 ml), anhydrous potassium carbonate (3.29 g) and hexamethylphosphoric acid triamide (2.07 g) was heated at 70–80° C. with stirring for 4.5 days. Then, the insoluble matter was filtered off and the filtrate was concentrated. Water was added to the residue and the mixture was extracted with ethyl acetate. The extract layer was dried over magnesium sulfate, then the solvent was distilled off, and the residue was applied to a silica gel column (50 g). Elution with chloroform-methanol (10:1) and recrystallization from ethyl acetate-hexane gave 2.4 g of 2,3-dimethyl-4-(2,2,3,3,3-pentafluoropropoxy)pyridine-1-oxide as colorless needles. Melting point 148–149° C.

The following compounds (VII) were produced from the corresponding compounds (V) in the same manner as above.

| Compounds (VII) | | | |
|---|---|---|---|
| $R^3$ | $R^5$ | $R^4$ | Melting point (° C.) |
| $CH_3$ | H | $OCH_2CF_3$ | 131.0–131.5 |
| Note 1) H | H | $OCH_2CH_2CH_3$ | Oil |
| Note 2) $CH_3$ | H | $OCH_2CH_2CH_3$ | Oil |

Note 1): NMR spectrum (CDCl$_3$) δ: 1.01 (3H, t, J = 7 Hz), 1.81 (2H, m), 2.50 (3H, s), 3.93 (2H, t, J = 7 Hz), 6.50–6.80 (2H, m), 8.10 (1H, d, J = 7 Hz)
Note 2): NMR spectrum (CDCl$_3$) δ: 1.07 (3H, t, J = 7.5 Hz), 1.65–2.02 (2H, m), 2.21 (3H, s), 2.52 (3H, s), 3.99 (2H, t, J = 6 Hz), 6.68 (1H, d, J = 6 Hz), 8.15 (1H, d, J = 6 Hz)

REFERENCE EXAMPLE 2

Concentrated sulfuric acid (2 drops) was added to a solution of 2,3-dimethyl-4-(2,2,3,3,3-pentafluoropropoxy)pyridine-1-oxide (2.5 g) in acetic anhydride (8 ml) and the mixture was stirred at 110° C. for 2 hours and then concentrated. The residue was dissolved in methanol (30 ml), 2 N aqueous sodium hydroxide (20 ml) was added, and the mixture was stirred at room temperature for 2 hours. After concentration, water was added to the residue and the mixture was extracted with ethyl acetate. The extract was dried over magnesium sulfate, the solvent was then distilled off, and the residue was applied to a silica gel (50 g) column. Elution with chloroform-methanol (10:1) and recrystallization from isopropyl ether gave 1.6 g of 2-hydroxymethyl-3-methyl-4-(2,2,3,3,3-pentafluoropropoxy)pyridine as a brown oil.
NMR spectrum (CDCl$_2$) δ: 2.07 (3H, s), 4.28 (1H, brs), 4.49 (2H, t, J=12 Hz), 4.67 (2H, s), 6.69 (1H, d, J=5 Hz), 8.34 (1H, d, J=5 Hz)

The following compounds (IX) were produced from the corresponding compounds (VII) in the same manner as mentioned above.

| Compounds (IX) | | | |
|---|---|---|---|
| $R^3$ | $R^5$ | $R^4$ | Melting point (° C.) |
| $CH_3$ | H | $OCH_2CF_3$ | 93.5–94.0 |
| Note 1) H | H | $OCH_2CH_2CH_3$ | Oil |
| Note 2) $CH_3$ | H | $OCH_2CH_2CH_3$ | Oil |

Note 1) NMR spectrum (CDCl$_3$) δ: 1.0 (3H, t, J = 7.5 Hz), 1.79 (2H, m), 3.92 (2H, t, J = 6 Hz), 4.51–4.90 (1H, br), 4.68 (2H, s), 6.68 (1H, dd, J = 2 and 6 Hz), 6.80 (1H, d, J = 2 Hz), 8.28 (1H, d, J = 6 Hz)
Note 2) NMR spectrum (CDCl$_3$) δ: 1.03 (3H, t, J = 7.5 Hz), 1.82 (2H, m), 2.02 (3H, s), 3.95 (2H, t, J = 6 Hz), 4.62 (2H, s), 5.20 (1H, brd, s), 6.68 (1H, d, J = 6 Hz), 8.25 (1H, d, J = 6 Hz)

REFERENCE EXAMPLE 3

Thionyl chloride (0.2 ml) was added to a solution of 2-hydroxymethyl-3-methyl-4-(2,2,3,3,3-pentafluoropropoxy)pyridine (350 mg) in chloroform (10 ml) and the mixture was refluxed for 30 minutes and then concentrated. The residue was dissolved in methanol (5 ml) and the solution was added to a mixture of 2-mercaptobenzimidazole (200 mg), 28% sodium methoxide solution (1 ml) and methanol (6 ml). The resultant mixture was refluxed for 30 minutes. The methanol was distilled off, water was added to the residue, and the mixture was extracted with ethyl acetate. The extract was washed with dilute sodium hydroxide solution and dried over magnesium sulfate. The solvent was then distilled off, and the residue was applied to a silica gel (20 g) column. Elution with ethyl acetate-hexane (2:1) and recrystallization from ethyl acetate-hexane gave 370 mg of 2-[[3-methyl-4-(2,2,3,3,3-pentafluoropropoxy)-2-pyridyl]methylthio]benzimidazole hemihydrate as colorless plates. Melting point 145–146° C.

The following compounds (II) were produced by reacting the compound (III) with the corresponding compound (IV) in the same manner as mentioned above.

| Compounds (II) | | | | | |
|---|---|---|---|---|---|
| $R^1$ | $R^2$ | $R^3$ | $R^5$ | $R^4$ | Melting point (° C.) |
| H | H | $CH_3$ | H | $OCH_2CF_3$ | 149–150 |
| H | H | H | H | $OCH_2CH_2CH_3$ | 84–86 |
| Note) H | H | $CH_3$ | H | $OCH_2CH_2CH_3$ | Oil |

Note) NMR spectrum (CDCl$_3$) δ: 0.98 (3H, t, J = 7.5 Hz), 1.54–1.92 (2H, m), 2.15 (3H, s), 3.80 (2H, t, J = 6 Hz), 4.43 (2H, s), 6.55 (1H, d, J = 6 Hz), 7.09 (2H, m), 7.50 (2H, m), 8.21 (1H, d, J = 6 Hz)

REFERENCE EXAMPLE 4

A solution of m-chloroperbenzoic acid (1.3 g) in chloroform (15 ml) was added dropwise to a solution of 2-[[3-methyl-4-(2,2,3,3,3-pentafuloropropoxy)-2-pyridyl]methylthio]benzimidazole (2.2 g) in chloroform (20 ml) with ice cooling over 30 minutes and, then, the reaction mixture was washed with saturated aqueous sodium hydrogen carbonate solution, dried over magnesium sulfate and concentrated. The concentrate was applied to a silica gel (50 g) column. Elution with ethyl acetate and recrystallization from acetone-isopropyl ether gave 1.78 g of 2-[[3-methyl-4-(2,2,3,3,3-pentafluoropropoxy)-2-pyridyl]methylsulfinyl]benzimidazole [hereinafter sometimes referred to as compound (A)] as pale yellow prisms. Melting point 161–163° C. (decomposition).

The following compounds (I) [hereinafter sometimes referred to as compound (B), compound (C) and compound (D), respectively] were produced in the same manner from the corresponding compounds (II).

| Compounds (I) | | | | | |
|---|---|---|---|---|---|
| | $R^1$ | $R^2$ | $R^3$ | $R^5$ | $R^4$ | Melting point (° C.) |
| (B) | H | H | $CH_3$ | H | $OCH_2CF_3$ | 178–182 (decomp.) |
| (C) | H | H | H | H | $OCH_2CH_2CH_3$ | 123–125 (decomp.) |
| (D) | H | H | $CH_3$ | H | $OCH_2CH_2CH_3$ | 81–83 |

EXAMPLE 1

Of the components given below, the compound (A), magnesium hydroxide, L-cysteine, corn starch and lactose were mixed together, then microcrystalline cellulose, light silicic anhydride and magnesium stearate, each in half the intended amount, were added. After sufficient admixing, the mixture was compression-molded on a dry granulator (roller compactor; Freund, Japan. The compressed mass was ground in a mortar, the resultant granular mass was passed through a round sieve (16 mesh). The remaining portions of microcrystalline cellulose, light silicic anhydride and magnesium stearate were added to the sieved mass and, after admixing, the whole mixture was made up into tablets each weighing 250 mg on a rotary tableting machine (Kikusui Seisakusho, Japan).

| Composition per tablet: | |
| --- | --- |
| Compound (A) | 50 mg |
| Magnesium hydroxide | 30 mg |
| L-Cysteine | 20 mg |
| Corn starch | 20 mg |
| Lactose | 65.2 mg |
| Microcrystalline cellulose | 60 mg |
| Light silicic anhydride | 1.8 mg |
| Magnesium stearate | 3.0 mg |
| Total | 250.0 mg |

EXAMPLE 2

Tablets were produced in the same manner as in Example 1 except that omeprazole (Note) was used instead of the compound (A).

Note: 5-Methoxy-2-[(4-methoxy-3,5-dimethyl-2-pyridyl)methylsulfinyl]benzimidazole

EXAMPLE 3

Of the components given below, the compound (B), precipitated calcium carbonate, corn starch, lactose and hydroxypropylcellulose were mixed together, water was added, and the mixture was kneaded, then dried in vacuum at 40° C. for 16 hours, ground in a mortar and passed through a 16-mesh sieve to give granules. To this was added magnesium stearate and the resultant mixture was made up into tablets each weighing 200 mg on a rotary tableting machine (Kikusui Seisakusho, Japan).

| Composition per tablet: | |
| --- | --- |
| Compound (B) | 30 mg |
| Precipitated calcium carbonate | 50 mg |
| Corn starch | 40 mg |
| Lactose | 73.4 mg |
| Hydroxypropylcellulose | 6 mg |
| Magnesium stearate | 0.6 mg |
| Water | (0.05 ml) |
| Total | 200.0 mg |

EXAMPLE 4

Tablets were produced in the same manner as in Example 3 except that timoprazole (Note) was used instead of the compound (B).

Note: 2-[(2-Pyridyl)methylsulfinyl]benzimidazole

EXAMPLE 5

The ingredients given below were mixed well in the porportions given below, water was added, and the mixture was kneaded and granulated in an extruder granulator (Kikusui Seisakusho; screen size 1.0 mm o). The granules were immediately converted to spherical form in a spheronizer (Fuji Powder's Marumerizer, Japan; 1,000 rpm). The spherical granules were then dried under vacuum at 40° C. for 16 hours and passed through round sieves to give 12- to 42-mesh granules.

| Composition per 200 mg of granules | |
| --- | --- |
| Compound (B) | 30 mg |
| Heavy magnesium carbonate | 20 mg |
| Corn starch | 80 mg |
| Microcrystalline cellulose | 20 mg |
| Carboxymethylcellulose calcium | 10 mg |
| Hydroxypropylcellulose | 10 mg |
| Pluronic F68 | 4 mg |
| Lactose | 26 mg |
| Water | (0.1 ml) |
| Total | 200 mg |

EXAMPLE 6

Granules were produced in the same manner as in Example 5 except that the compound (D) was used instead of the compound (B).

EXAMPLE 7

Enteric granules were produced by coating the granules obtained in Example 3 with an enteric coating composition specified below using a fluidized bed granulator (Okawara, Japan) under conditions such that the inlet air temperature was 50° C. and the granule temperature was 40° C. No. 1 hard capsules were filled with the enteric granules thus obtained in an amount of 260 mg per capsule using a capsule filling machine (Parke-Davis, U.S.A.).

| Enteric coating composition: | |
| --- | --- |
| Eudragit L-30D | 138 mg (solids 41.4 mg) |
| Talc | 4.1 mg |
| Polyethylene glycol 6000 | 12.4 mg |
| Tween 80 | 2.1 mg |
| Water | 276 µl |
| Composition of enteric granules: | |
| Granules of Example 5 | 200 mg |
| Enteric coat | 60 mg |
| Total | 260 mg |
| Composition per capsule: | |
| Enteric granules | 260 mg |
| No. 1 hard capsule | 76 mg |
| Total | 336 mg |

EXAMPLE 8

Of the components given below, the compound (B), magunesium carbonate, socrose, corn starch and crystalline cellulose were thoroughly mixed together to obtain dusting powder.

Nonpareils were put on a centrifugal fluidized coating-granulatar (CF-360 Freund, Japan) and then coated with the dusting powder as described above, while spraying hydroxypropylcellulose solution [4% (w/w)], to give spherical granules. The spherical granules were dried in vacuum at 40° C. for 16 hours and then passed through round sieves to give 12 to 32-mesh granules.

| Composition per 190 mg of granules: | |
|---|---|
| Nonpareil | 75 mg |
| Compound (B) | 15 mg |
| Magnesiun carbonate | 15 mg |
| Sucrose | 29 mg |
| Corn starch | 27 mg |
| Crystalline cellulose | 27 mg |
| Hydroxypropylcellulose [Hydroxypropoxy group content: 53.4–77.5%] | 2 mg |
| Water | (0.05 ml) |
| Total | 190 mg |

EXAMPLE 9

Enteric granules were produced by coating the granules obtained in Example 8 with an enteric coatig composition specified below usig a fluidized bed granulator (Okawara, Japan) under conditions such that inlet air temperature was 50° C. and the granule temperature was 40° C. No. 2 hard capsules were filled with the enteric granules thus obtained in an amount of 240 mg per capsule using a capsule filling machine (Parke-Davis, USA).

| Enteric coating composition: | |
|---|---|
| Eudragit L-30D | 104.7 mg (solids 31.4 mg) |
| Talc | 9.6 mg |
| Polyethylene glycol 6000 | 3.2 mg |
| Tween 80 | 1.6 mg |
| Titanium oxide | 4.2 mg |
| Water | (220 µl) |
| Composition of enteric granules: | |
| Granules of Example 8 | 190 mg |
| Enteric coat | 50 mg |
| Total | 240 mg |
| Composition per capsule: | |
| Enteric granules | 240 mg |
| No. 2 hard capsule | 65 mg |
| Total | 305 mg |

EXAMPLE 10

| Composition 1: | |
|---|---|
| Compound (B) | 450 g |
| Magnesium carbonate | 450 g |
| Sucrose | 430 g |
| Corn starch | 450 g |
| Low substituted hydroxypropylcellulose [Hydroxypropoxy group content: 10.0–13.0% (w/w), average particle size: no more than 30 µm] | 450 g |
| Composition 2: | |
| Sucrose | 420 g |
| Corn starch | 360 g |
| Low substituted hydroxypropylcellulose [Hydroxypropoxy group content: 10.0–13.0% (w/w), average particle size: no more than 30 µm] | 360 g |

Ingredients of the above composition 1 and composition 2 were thoroughly mixed together to obtain dusting powder 1 and dusting powder 2, respectively.

2250 g of nonpareils were put on a centrifugal fluidized coating granulatar (CF-360 Freund, Japan) and then coated with the dusting powder 1, then with the dusting powder 2, while spraying 60 g of hydroxypropylcellulose in water (2000 ml) to give spherical granules.

The spherical granules were dried in vacuum at 40° C. for 16 hours and then passed through round sieve to give 12 to 32-mesh granules.

EXAMPLE 11

Enteric granules were produced by coating 3800 g of the granules obtained in Example 10 with an enteric coating composition specified below using a fluidized bed granulatar (Okawara, Japan) under conditions such that inlet air temperature was 50° C. and the granule temperature was 40° C. No. 2 hard capsules were filled with the enteric granules thus obtained in an amount of 240 mg per capsule using a filling machine (Parke-Davis, USA).

| Enteric coating composition: | |
|---|---|
| Eudragit L30D-55 | 628 g |
| Talc | 192 g |
| Polyethylene glycol 6000 | 64 g |
| Titanium oxide | 64 g |
| Tween 80 | 32 g |
| Water | 4400 ml |
| Composition per capsule: | |
| Enteric granules | 240 mg |
| No. 2 hard capsule | 65 mg |

EXPERIMENTAL EXAMPLE 1a

The ingredients given below were mixed well in the proportions given below, water was added, and the mixture was kneaded and granulated in an extruder granulator (Kikusui Seisakusho; screen size 1.0 mm φ). The granules were immediately converted to spherical form in a spheronizer (Fuji Powder's Marumerizer, Japan; 1,000 rpm). The spherical granules were then dried under vacuum at 40° C. for 16 hours and passed through round sieves to give 12- to 42-mesh granules.

| Composition per 200 mg of granules | |
|---|---|
| Compound (B) | 30 mg |
| Heavy magnesium carbonate | 20 mg |
| Corn starch | 80 mg |
| Microcrystalline cellulose | 20 mg |
| Carboxymethylcellulose calcium | 10 mg |
| Hydroxypropylcellulose | 10 mg |
| Pluronic F68 | 4 mg |
| Lactose | 26 mg |
| Water | (0.1 ml) |
| Total | 200 mg |

After storage at 50° C. and 75% RH for 1 week, the granules were observed for changes in appearance. The granules of this example showed no change in appearance.

EXPERIMENTAL EXAMPLE 1b

The ingredients given below were mixed well in the proportions given below, water was added, and the mixture was kneaded and granulated in an extruder granulator (Kikusui Seisakusho; screen size 1.0 mm φ). The granules were immediately converted to spherical form in a spheronizer (Fuji Powder's Marumerizer, Japan; 1,000 rpm). The spherical granules were then dried under vacuum at 40° C. for 16 hours and passed through round sieves to give 12- to 42-mesh granules.

| Composition per 200 mg of granules | |
|---|---|
| Compound (B) | 30 mg |
| Magnesium Oxide | 20 mg |
| Corn starch | 80 mg |
| Microcrystalline cellulose | 20 mg |
| Carboxymethylcellulose calcium | 10 mg |
| Hydroxypropylcellulose | 10 mg |
| Pluronic F68 | 4 mg |
| Lactose | 26 mg |
| Water | (0.1 ml) |
| Total | 200 mg |

After storage at 50° C. and 75% RH for 1 week, the granules were observed for changes in appearance. The granules of this example showed no change in appearance.

EXPERIMENTAL EXAMPLE 1c

The ingredients given below were mixed well in the proportions given below, water was added, and the mixture was kneaded and granulated in an extruder granulator (Kikusui Seisakusho; screen size 1.0 mm φ). The granules were immediately converted to spherical form in a spheronizer (Fuji Powder's Marumerizer, Japan; 1,000 rpm). The spherical granules were then dried under vacuum at 40° C. for 16 hours and passed through round sieves to give 12- to 42-mesh granules.

| Composition per 200 mg of granules | |
|---|---|
| Compound (B) | 30 mg |
| Magnesium Metasilicate Aluminate | 20 mg |
| Corn starch | 80 mg |
| Microcrystalline cellulose | 20 mg |
| Carboxymethylcellulose calcium | 10 mg |
| Hydroxypropylcellulose | 10 mg |
| Pluronic F68 | 4 mg |
| Lactose | 26 mg |
| Water | (0.1 ml) |
| Total | 200 mg |

After storage at 50° C. and 75% RH for 1 week, the granules were observed for changes in appearance. The granules of this example showed no change in appearance.

EXPERIMENTAL EXAMPLE 1d

The ingredients given below were mixed well in the proportions given below, water was added, and the mixture was kneaded and granulated in an extruder granulator (Kikusui Seisakusho; screen size 1.0 mm φ). The granules were immediately converted to spherical form in a spheronizer (Fuji Powder's Marumerizer, Japan; 1,000 rpm). The spherical granules were then dried under vacuum at 40° C. for 16 hours and passed through round sieves to give 12- to 42-mesh granules.

| Composition per 200 mg of granules | |
|---|---|
| Compound (B) | 30 mg |
| Synthetic Hydrotalcite | 20 mg |
| Corn starch | 80 mg |
| Microcrystalline cellulose | 20 mg |
| Carboxymethylcellulose calcium | 10 mg |
| Hydroxypropylcellulose | 10 mg |
| Pluronic F68 | 4 mg |
| Lactose | 26 mg |
| Water | (0.1 ml) |
| Total | 200 mg |

After storage at 50° C. and 75% RH for 1 week, the granules were observed for changes in appearance. The granules of this example showed no change in appearance.

EXPERIMENTAL EXAMPLE 1e

The ingredients given below were mixed well in the proportions given below, water was added, and the mixture was kneaded and granulated in an extruder granulator (Kikusui Seisakusho; screen size 1.0 mm φ). The granules were immediately converted to spherical form in a spheronizer (Fuji Powder's Marumerizer, Japan; 1,000 rpm). The spherical granules were then dried under vacuum at 40° C. for 16 hours and passed through round sieves to give 12- to 42-mesh granules.

| Composition per 200 mg of granules | |
|---|---|
| Compound (B) | 30 mg |
| Aluminum magnesium hydroxide | 20 mg |
| Corn starch | 80 mg |
| Microcrystalline cellulose | 20 mg |
| Carboxymethylcellulose calcium | 10 mg |
| Hydroxypropylcellulose | 10 mg |
| Pluronic F68 | 4 mg |
| Lactose | 26 mg |
| Water | (0.1 ml) |
| Total | 200 mg |

After storage at 50° C. and 75% RH for 1 week, the granules were observed for changes in appearance. The granules of this example showed no change in appearance.

EXPERIMENTAL EXAMPLE 1f

The ingredients given below were mixed well in the proportions given below, water was added, and the mixture was kneaded and granulated in an extruder granulator (Kikusui Seisakusho; screen size 1.0 mm φ). The granules were immediately converted to spherical form in a spheronizer (Fuji Powder's Marumerizer, Japan; 1,000 rpm). The spherical granules were then dried under vacuum at 40° C. for 16 hours and passed through round sieves to give 12- to 42-mesh granules.

| Composition per 200 mg of granules | |
|---|---|
| Compound (B) | 30 mg |
| Magnesium silicate | 20 mg |
| Corn starch | 80 mg |
| Microcrystalline cellulose | 20 mg |

-continued

| Composition per 200 mg of granules | |
|---|---|
| Carboxymethylcellulose calcium | 10 mg |
| Hydroxypropylcellulose | 10 mg |
| Pluronic F68 | 4 mg |
| Lactose | 26 mg |
| Water | (0.1 ml) |
| Total | 200 mg |

After storage at 50° C. and 75% RH for 1 week, the granules were observed for changes in appearance. The granules of this example showed no change in appearance.

EXPERIMENTAL EXAMPLE 1g

The ingredients given below were mixed well in the proportions given below, water was added, and the mixture was kneaded and granulated in an extruder granulator (Kikusui Seisakusho; screen size 1.0 mm φ). The granules were immediately converted to spherical form in a spheronizer (Fuji Powder's Marumerizer, Japan; 1,000 rpm). The spherical granules were then dried under vacuum at 40° C. for 16 hours and passed through round sieves to give 12- to 42-mesh granules.

| Composition per 200 mg of granules | |
|---|---|
| Compound (B) | 30 mg |
| Precipitated calcium carbonate | 20 mg |
| Corn starch | 80 mg |
| Microcrystalline cellulose | 20 mg |
| Carboxymethylcellulose calcium | 10 mg |
| Hydroxypropylcellulose | 10 mg |
| Pluronic F68 | 4 mg |
| Lactose | 26 mg |
| Water | (0.1 ml) |
| Total | 200 mg |

After storage at 50° C. and 75% RH for 1 week, the granules were observed for changes in appearance. The granules of this example showed no change in appearance.

EXPERIMENTAL EXAMPLE 1h

The ingredients given below were mixed well in the proportions given below, water was added, and the mixture was kneaded and granulated in an extruder granulator (Kikusui Seisakusho; screen size 1.0 mm φ). The granules were immediately converted to spherical form in a spheronizer (Fuji Powder's Marumerizer, Japan; 1,000 rpm). The spherical granules were then dried under vacuum at 40° C. for 16 hours and passed through round sieves to give 12- to 42-mesh granules.

| Composition per 200 mg of granules | |
|---|---|
| Compound (B) | 30 mg |
| Magnesium hydroxide | 20 mg |
| Corn starch | 80 mg |
| Microcrystalline cellulose | 20 mg |
| Carboxymethylcellulose calcium | 10 mg |
| Hydroxypropylcellulose | 10 mg |
| Pluronic F68 | 4 mg |
| Lactose | 26 mg |
| Water | (0.1 ml) |
| Total | 200 mg |

After storage at 50° C. and 75% RH for 1 week, the granules were observed for changes in appearance. The granules of this example showed no change in appearance.

EXPERIMENTAL EXAMPLE 1i

The ingredients given below were mixed well in the proportions given below, water was added, and the mixture was kneaded and granulated in an extruder granulator (Kikusui Seisakusho; screen size 1.0 mm φ). The granules were immediately converted to spherical form in a spheronizer (Fuji Powder's Marumerizer, Japan; 1,000 rpm). The spherical granules were then dried under vacuum at 40° C. for 16 hours and passed through round sieves to give 12- to 42-mesh granules.

| Composition per 200 mg of granules | |
|---|---|
| Compound (B) | 30 mg |
| Sodium carbonate | 20 mg |
| Corn starch | 80 mg |
| Microcrystalline cellulose | 20 mg |
| Carboxymethylcellulose calcium | 10 mg |
| Hydroxypropylcellulose | 10 mg |
| Pluronic F68 | 4 mg |
| Lactose | 26 mg |
| Water | (0.1 ml) |
| Total | 200 mg |

After storage at 50° C. and 75% RH for 1 week, the granules were observed for changes in appearance. The granules of this example showed a moderate change in appearance to yellow.

EXPERIMENTAL EXAMPLE 1j

The ingredients given below were mixed well in the proportions given below, water was added, and the mixture was kneaded and granulated in an extruder granulator (Kikusui Seisakusho; screen size 1.0 mm φ). The granules were immediately converted to spherical form in a spheronizer (Fuji Powder's Marumerizer, Japan; 1,000 rpm). The spherical granules were then dried under vacuum at 40° C. for 16 hours and passed through round sieves to give 12- to 42-mesh granules.

| Composition per 200 mg of granules | |
|---|---|
| Compound (B) | 30 mg |
| Potassium carbonate | 20 mg |
| Corn starch | 80 mg |
| Microcrystalline cellulose | 20 mg |
| Carboxymethylcellulose calcium | 10 mg |
| Hydroxypropylcellulose | 10 mg |
| Pluronic F68 | 4 mg |
| Lactose | 26 mg |
| Water | (0.1 ml) |
| Total | 200 mg |

After storage at 50° C. and 75% RH for 1 week, the granules were observed for changes in appearance. The granules of this example showed a moderate change in appearance to yellow.

EXPERIMENTAL EXAMPLE 1k

The ingredients given below were mixed well in the proportions given below, water was added, and the mixture was kneaded and granulated in an extruder granulator (Kikusui Seisakusho; screen size 1.0 mm φ). The granules were immediately converted to spherical form in a spheronizer (Fuji Powder's Marumerizer, Japan; 1,000 rpm). The spherical granules were then dried under vacuum at 40° C. for 16 hours and passed through round sieves to give 12- to 42-mesh granules.

| Composition per 200 mg of granules | |
| --- | --- |
| Compound (B) | 30 mg |
| Sodium hydrogen carbonate | 20 mg |
| Corn starch | 80 mg |
| Microcrystalline cellulose | 20 mg |
| Carboxymethylcellulose calcium | 10 mg |
| Hydroxypropylcellulose | 10 mg |
| Pluronic F68 | 4 mg |
| Lactose | 26 mg |
| Water | (0.1 ml) |
| Total | 200 mg |

After storage at 50° C. and 75% RH for 1 week, the granules were observed for changes in appearance. The granules of this example showed a moderate change in appearance to yellow.

EXPERIMENTAL EXAMPLE 1l

The ingredients given below were mixed well in the proportions given below, water was added, and the mixture was kneaded and granulated in an extruder granulator (Kikusui Seisakusho; screen size 1.0 mm φ). The granules were immediately converted to spherical form in a spheronizer (Fuji Powder's Marumerizer, Japan; 1,000 rpm). The spherical granules were then dried under vacuum at 40° C. for 16 hours and passed through round sieves to give 12- to 42-mesh granules.

| Composition per 200 mg of granules | |
| --- | --- |
| Compound (B) | 30 mg |
| Magnesium chloride | 20 mg |
| Corn starch | 80 mg |
| Microcrystalline cellulose | 20 mg |
| Carboxymethylcellulose calcium | 10 mg |
| Hydroxypropylcellulose | 10 mg |
| Pluronic F68 | 4 mg |
| Lactose | 26 mg |
| Water | (0.1 ml) |
| Total | 200 mg |

After storage at 50° C. and 75% RH for 1 week, the granules were observed for changes in appearance. The granules of this example showed a severe in appearance, to violet.

EXPERIMENTAL EXAMPLE 1m

The ingredients given below were mixed well in the proportions given below, water was added, and the mixture was kneaded and granulated in an extruder granulator (Kikusui Seisakusho; screen size 1.0 mm φ). The granules were immediately converted to spherical form in a spheronizer (Fuji Powder's Marumerizer, Japan; 1,000 rpm). The spherical granules were then dried under vacuum at 40° C. for 16 hours and passed through round sieves to give 12- to 42-mesh granules.

| Composition per 200 mg of granules | |
| --- | --- |
| Compound (B) | 30 mg |
| Magnesium sulfate | 20 mg |
| Corn starch | 80 mg |
| Microcrystalline cellulose | 20 mg |
| Carboxymethylcellulose calcium | 10 mg |
| Hydroxypropylcellulose | 10 mg |
| Pluronic F68 | 4 mg |
| Lactose | 26 mg |
| Water | (0.1 ml) |
| Total | 200 mg |

After storage at 50° C. and 75% RH for 1 week, the granules were observed for changes in appearance. The granules of this example showed a severe change in appearance, to violet.

EXPERIMENTAL EXAMPLE 1n

The ingredients given below were mixed well in the proportions given below, water was added, and the mixture was kneaded and granulated in an extruder granulator (Kikusui Seisakusho; screen size 1.0 mm φ). The granules were immediately converted to spherical form in a spheronizer (Fuji Powder's Marumerizer, Japan; 1,000 rpm). The spherical granules were then dried under vacuum at 40° C. for 16 hours and passed through round sieves to give 12- to 42-mesh granules.

| Composition per 200 mg of granules | |
| --- | --- |
| Compound (B) | 30 mg |
| Calcium chloride | 20 mg |
| Corn starch | 80 mg |
| Microcrystalline cellulose | 20 mg |
| Carboxymethylcellulose calcium | 10 mg |
| Hydroxypropylcellulose | 10 mg |
| Pluronic F68 | 4 mg |
| Lactose | 26 mg |
| Water | (0.1 ml) |
| Total | 200 mg |

After storage at 50° C. and 75% RH for 1 week, the granules were observed for changes in appearance. The granules of this example showed a severe change in appearance, to violet.

EXPERIMENTAL EXAMPLE 1o

The ingredients given below were mixed well in the proportions given below, water was added, and the mixture was kneaded and granulated in an extruder granulator (Kikusui Seisakusho; screen size 1.0 mm φ). The granules were immediately converted to spherical form in a spheronizer (Fuji Powder's Marumerizer, Japan; 1,000 rpm). The spherical granules were then dried under vacuum at 40° C. for 16 hours and passed through round sieves to give 12- to 42-mesh granules.

| Composition per 200 mg of granules | |
|---|---|
| Compound (B) | 30 mg |
| aluminum silicate | 20 mg |
| Corn starch | 80 mg |
| Microcrystalline cellulose | 20 mg |
| Carboxymethylcellulose calcium | 10 mg |
| Hydroxypropylcellulose | 10 mg |
| Pluronic F68 | 4 mg |
| Lactose | 26 mg |
| Water | (0.1 ml) |
| Total | 200 mg |

After storage at 50° C. and 75% RH for 1 week, the granules were observed for changes in appearance. The granules of this example showed a moderate change in appearance, to violet.

EXPERIMENTAL EXAMPLE 1p

The ingredients given below were mixed well in the proportions given below, water was added, and the mixture was kneaded and granulated in an extruder granulator (Kikusui Seisakusho; screen size 1.0 mm φ). The granules were immediately converted to spherical form in a spheronizer (Fuji Powder's Marumerizer, Japan; 1,000 rpm). The spherical granules were then dried under vacuum at 40° C. for 16 hours and passed through round sieves to give 12- to 42-mesh granules.

| Composition per 200 mg of granules | |
|---|---|
| Compound (B) | 30 mg |
| Corn starch | 80 mg |
| Microcrystalline cellulose | 20 mg |
| Carboxymethylcellulose calcium | 10 mg |
| Hydroxypropylcellulose | 10 mg |
| Pluronic F68 | 4 mg |
| Lactose | 46 mg |
| Water | (0.1 ml) |
| Total | 200 mg |

After storage at 50° C. and 75% RH for 1 week, the granules were observed for changes in appearance. The granules of this example showed a severe change in appearance, to violet.

EXPERIMENTAL EXAMPLE 2

Granules were produced in the same manner as in Example 5 except that the compound (A), the compound (C), the compound (D), omeprazole or timoprazole was used instead of the compound (B). After storage at 50° C. and 75% RH for 1 week, they were observed for changes in appearance. As a control to each composition, granules were also produced in the same manner except that lactose was used instead of heavy magnesium carbonate and stored under the same conditions.

| Compound | | Additive | Changes in appearance after 1 week at 50° C. and 75% RH |
|---|---|---|---|
| Compound (A) | Invention: | Heavy magnesium carbonate | − |
| | Control: | Lactose | ++ |
| Omeprazole | Invention: | Heavy magnesium carbonate | − |
| | Control: | Lactose | ++ |
| Timoprazole | Invention: | Heavy magnesium carbonate | − |
| | Control: | Lactose | ++ |
| Compound (C) | Invention: | Heavy magnesium carbonate | − |
| | Control: | Lactose | ++ |
| Compound (D) | Invention: | Heavy magnesium carbonate | − |
| | Control: | Lactose | ++ |

Notes:
−: No changes
++: Severely

As is evident from the above results, the pharmaceutical compositions of the invention were all stable whether the active ingredient was the compound (A), omeprazole, timoprazole, the compound (C) or the compound (D).

EXPERIMENTAL EXAMPLE 3

Pharmaceutical compositions were produced in the same manner as in Examples 3 and 5 except that different basic inorganic Mg or Ca salts were used or that lactose was used as a control, and Example 6. After strage at 50° C. and 75% RH for 1 week or at 40° C. for 6 months, the compositions were observed for changes in appearance and for active ingredient content (residual percentage).

TABLE 2

| | Additive | | Initial | 50° C., 75% RH, 1 week | 40° C., 6 months |
|---|---|---|---|---|---|
| Tablets made by the procedure of Example 3 | | | | | |
| Invention | Heavy magnesium carbonate | Appearance | White | No change | No change |
| | | Content | 100% | 98.0% | 99.5% |
| | Precipitated calcium carbonate | Appearance | White | No change | No change |
| | | Content | 100% | 97.4% | 96.5% |
| | Magnesium silicate | Appearance | White | No change | No change |
| | | Content | 100% | 94.5% | 95.0% |
| Control | No addition (lactose) | Appearance | Pale violet | Dark violet | Dark violet |
| | | Content | 100% | 73.5% | 82.1% |
| Granudles made by the procedure of Example 5 | | | | | |
| Invention | Heavy magnesium carbonate | Appearance | White | No change | No change |
| | | Content | 100% | 98.2% | 99.1% |
| | Precipitate calcium | Appearance | White | No change | No change |

TABLE 2-continued

|  | Additive |  | Initial | 50° C., 75% RH, 1 week | 40° C., 6 months |
|---|---|---|---|---|---|
|  | carbonate | Content | 100% | 97.2% | 98.6% |
|  | Magnesium oxide | Appearance | White | No change | No change |
|  |  | Content | 100% | 99.4% | 99.0% |
| Control | No addition (lactose) | Appearance | Pale violet | Dark violet | Dark violet |
|  |  | Content | 100% | 84.2% | 89.4% |
|  | Capsules of Example 7 |  |  |  |  |
| Invention | Heavy magnesium carbonate | Appearance | White | No change | No change |
|  |  | Content | 100% | 98.4% | 99.1% |

The above results clearly indicate that the compositions of the invention show no changes in appearance at all and are stable in terms of the active ingredient content.

We claim:

1. A stabilized pharmaceutical composition for the inhibition of gastric acid secretion, comprising:

an effective amount of a 2-[(2-pyridyl)methylsulfinyl]benzimidazole compound or a pharmaceutically acceptable salt thereof having gastric acid secretion inhibitory property;

a basic inorganic salt stabilizing agent, comprising sodium carbonate, in an amount effective to stabilize the composition, the benzimidazole compound or its salt being in contact with the stabilizing agent evenly; and an enteric coating for the composition.

2. A method of providing a gastric acid secretion inhibitory effect to a subject in need thereof, comprising:

orally administering to the subject a stabilized pharmaceutical composition, comprising:

an effective amount of a 2-[(2-pyridyl)methylsulfinyl]benzimidazole compound or a pharmaceutically acceptable salt thereof having a gastric acid secretion inhibitory property;

a basic inorganic salt stabilizing agent, comprising sodium carbonate, in an amount effective to stabilize the composition, the benzimidazole compound or its salt being in contact with the stabilizing agent evenly; and an enteric coating for the composition.

3. In a method of preparing a pharmaceutical composition for the inhibition of gastric acid secretion that contains a 2-[(2-pyridyl)methylsulfinyl]benzimidazole compound or a pharmaceutically acceptable salt thereof having a gastric acid secretion inhibitory property as an active ingredient, the improvement comprising admixing a basic inorganic salt stabilizing agent comprising sodium carbonate to be in even contact with the 2-[(2-pyridyl)methylsulfinyl]benzimidazole compound or pharmaceutically acceptable salt thereof, and providing an enteric coating.

* * * * *

UNITED STATES PATENT AND TRADEMARK OFFICE
CERTIFICATE OF CORRECTION

PATENT NO.    : 6,380,234 B1
DATED         : April 30, 2002
INVENTOR(S)   : Makino et al.

It is certified that error appears in the above-identified patent and that said Letters Patent is hereby corrected as shown below:

Column 1,
Line 37, "can" should read -- and --

Column 14,
Line 60, "socrose" should read -- sucrose --

Signed and Sealed this

Twenty-third Day of September, 2003

JAMES E. ROGAN
*Director of the United States Patent and Trademark Office*